United States Patent [19]

Hession, Jr.

[11] 4,292,970

[45] Oct. 6, 1981

[54] APPARATUS FOR INTRAVENOUS CATHETER STARTER

[76] Inventor: William M. Hession, Jr., 317 Lee Dr., Thibodaux, La. 70301

[21] Appl. No.: 115,123

[22] Filed: Jan. 24, 1980

[51] Int. Cl.$^3$ .............................................. A61M 5/00
[52] U.S. Cl. ................................. 128/214.4; 128/348; 128/DIG. 16
[58] Field of Search ................... 128/214, 214.4, 215, 128/221, 347

[56] References Cited

U.S. PATENT DOCUMENTS

| | | | |
|---|---|---|---|
| 3,348,544 | 10/1967 | Braun | 128/214.4 |
| 3,352,306 | 11/1967 | Hirsch | 128/214.4 |
| 3,714,945 | 2/1973 | Stanley | 128/214.4 |
| 4,191,186 | 3/1980 | Keeler | 128/214.4 |
| 4,193,400 | 3/1980 | Loveless et al. | 128/214.4 |

Primary Examiner—Dalton L. Truluck
Attorney, Agent, or Firm—Wilkinson, Mawhinney & Theibault

[57] ABSTRACT

This invention is directed to introducing a catheter tube into a vein over a vein puncture needle once vein puncture has been established by providing an upstanding flat drive plate secured to the hub of a catheter tube with its major axis transverse to the axis of the needle and catheter so a quick striking force may be thrust upon the plate to force the catheter into the vein over the vein puncture needle.

The potential energy of a compressed coiled spring or a resilient plastic member may supply the thrust energy to drive the upstanding flat drive plate and its entrained catheter tube forwardly over the vein puncture needle.

3 Claims, 12 Drawing Figures

APPARATUS FOR INTRAVENOUS CATHETER STARTER

TECHNICAL FIELD

My invention relates to intravenous catheter of the catheter needle inside type which provides structural modification of the teflon coated catheter to assure positive forward motion of the catheter over the needle after vein puncture has been made by the needle so the catheter can be advanced the distance necessary to establish the treatment desired, i.e. I.V. Therapy, without chancing premature withdrawal of the needle and losing the establishment of the vein puncture.

My invention according to my method of establishing I.V. therapy after locating and preparing the choosen vein, the starter puts gentle traction on the vein with the index finger of his left hand after which he grasps the I.V. placement needle with plastic outside catheter with the right hand with the right thumb on the top of the back flow chamber guard, the middle finger on underside of the chamber guard and the I.V. placement needle with plastic outside catheter should be held by these fingertips with the posterior chamber end of the I.V. placement needle with plastic outside cathether resting snugly against the inside fleshy part of the right hand. At this point, the tip of the right index finger is pressed into the upper side of the thumb about ½" from the end of the thumb. Now, the starter has a firm hold on the I.V. placement needle with plastic outside catheter and the right index finger is positioned to "fire". The starter inserts the pointed end of the I.V. placement needle with plastic outside catheter into the skin, then into the vein to a point where he feels the tip of the teflon catheter is within the vein wall. At this point, the starter freezes—he sees the backflow of blood into the backflow chamber and simply releases the right index finger. The index finger thrusts forward striking the posterior side of the "rigid plastic ridge" on the catheter. The rigid plastic ridge along with the teflon catheter are projected forward. The teflon catheter moves forward on the inside of the vein and the plastic ridge remains outside the surface of the skin. The steel needle remains stationary. The teflon catheter is now safely in position.

BACKGROUND ART

Heretofore catheters of the needle inside type have been known and good examples of same are U.S. Pat. Nos. 3,595,230 and 3,537,456. The best known art to me at the time of filing this application are the following additional U.S. Pat. Nos. 3,906,946; 3,572,334; 3,766,915; 2,137,132 and 3,916,892. However none of these have as few moving parts of simple construction to assure a quick introduction of the catheter as soon as vein puncture is established by a positive quick thrust of the catheter into the vein.

DISCLOSURE OF THE INVENTION

My invention deals with the inside needle I.V. placement needle with plastic outside catheter such as is described in U.S. Pat. No. 3,494,230. This type needle is widely used. My invention may be added to almost any I.V. placement needle with plastic outside catheter presently on the market, for it is a rigid plastic ridge that is unified with the hub of the catheter. When the two main bodies of the I.V. placement needle with plastic outside catheter are fitted together as one it could be any present I.V. placement needle with plastic outside catheter, except the rigid plastic ridge. With present I.V. placement needle with plastic outside catheters being used generally, the main disadvantage or difficulty is in threading the catheter into the vein. This procedure is difficult with present I.V. placement needle with plastic outside catheters for the reason that in using the fingers to move the catheter in place and changing hand position, the starter often accidentally withdraws the needle from the vein or perforates the vein wall. With my proposed invention, manipulation and movement are drastically reduced to one simple quick forward motion by the index finger. (However, with even the modified means of projecting the plastic ridge forward, such as the spring loaded type and others briefly mentioned above, the procedure would be even more simplified) The simple motion of the index finger striking the plastic ridge projects the catheter along the inside of the vein. A detailed description of this technique cuts down dramatically the amount of human dexterity and skill needed to thread the catheter along the vein.

BEST MODE FOR CARRYING OUT THE INVENTION

Figure 1:
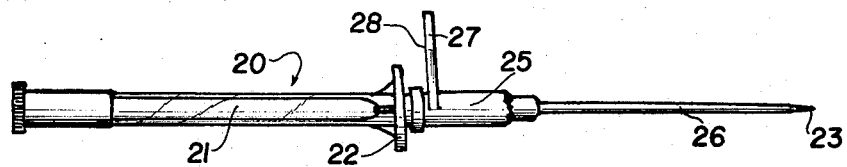
FIG. 1 is a side elevational view of an I.V. placement needle with plastic outside catheter constructed in accordance with my invention.
Figure 2:
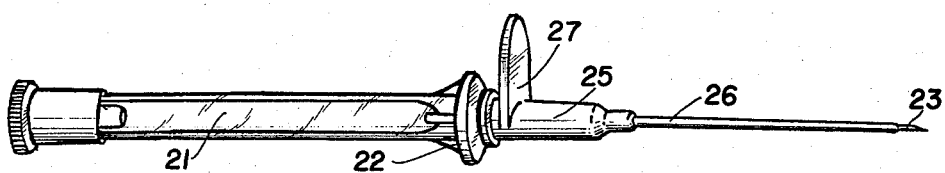
FIG. 2 is a perspective view of the I.V. placement needle with plastic outside catheter of FIG. 1.
Figure 3:
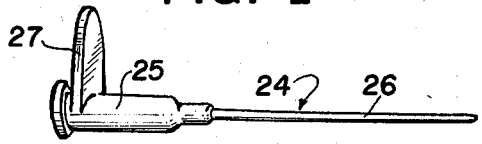
FIG. 3 is a perspective view of the I.V. placement needle with plastic outside catheter of FIGS. 1 and 2 with the teflon catheter removed from its concentric position over the vein puncture needle.
Figure 4:
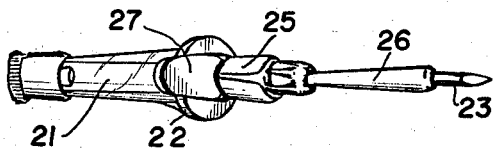
FIG. 4 is a top perspective view of the I.V. placement needle with plastic outside catheter of FIGS. 1 through 3 inclusive.

Referring now to FIGS. 1 through 4, 20 designates an I.V. placement needle with plastic outside catheter having a backflow chamber 21, a chamber guard 22 and a needle 23. Concentrically received over the needle 23 is a catheter 24 having a hub 25 and catheter tube 26. The hub 25 has secured thereto and upstanding therefrom a rigid plastic drive plate 27 having a broad striking flat surface 28 at a right angle to the axis of the catheter tube 26.

Figure 5:
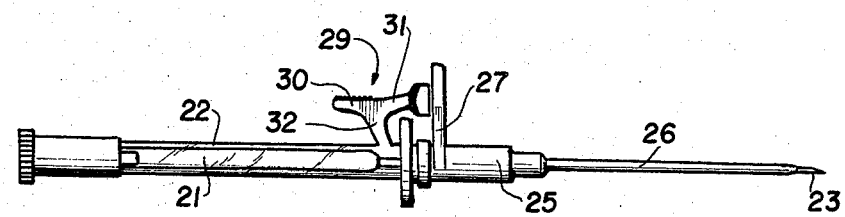
FIG. 5 is a side elevational view of a modified form of catheter showing the plastic hammer for driving the catheter forward after establishing vein puncture.

A modified form of my invention is shown in FIG. 5 which has secured thereto and upstanding from the top of the backflow chamber guard 22 a one piece three pronged plastic mechanical firing mechanism 29 having a cocking hammer 30, a firing arm 31 and a flexible bendable spring like support 32. The firing arm 31 is aligned to engage the broad striking flat surface of the rigid plastic drive plate 27.

Figure 6:
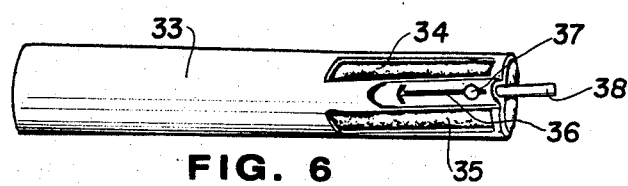
FIG. 6 is a top plan view of a modified I.V. placement needle with plastic outside catheter having a spring loaded hammer for driving the catheter forward.
Figure 7:
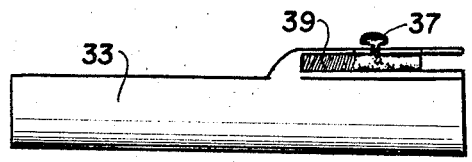
FIG. 7 is a side elevational view of the I.V. placement needle with plastic outside catheter of FIG. 6 in its cocked position.
Figure 8:
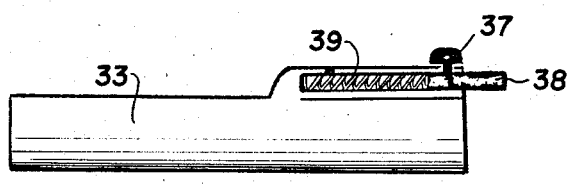
FIG. 8 is a view similar to FIG. 7 with the hammer in the discharged condition.

A further modified form of the invention as shown in FIGS. 6 through 8 inclusive has a modified form for firing tube 26 forward over the needle 23. A cylindrical chamber 33 is received over the backflow chamber 21 and has openings 34, 35 therethrough for viewing backflow for signs of vein puncture. Located centrally of the cylindrical chamber 33 is a T-slot 36 in which rides a trigger pin 37 for controlling a plunger 38 which is spring loaded. Upon aligning the pin 37 with the leg of the T-slot 36 the spring 39 will thrust the plunger 38 forwardly to engage the rigid plastic drive plate 27 and its entrained catheter forward after vein puncture has been established.

Referring now to FIGS. 9 through 12, a further modified form of the invention is shown for use with the I.V. placement needle with plastic outside catheter of FIGS. 1 through 4. A plastic slide 40 fits in the groove 41 and has an elevated thumb tab 42 on its posterior end.

Figure 12:
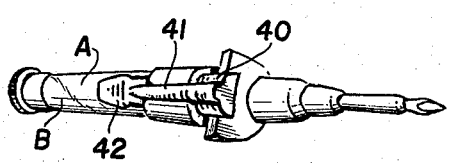
FIG. 12 is a top perspective view of the modified I.V. placement needle with plastic outside catheter assembled from the parts of FIGS. 9 through 11 inclusive.

The thumb tab 42 can be moved forward with the tip of the index finger and in turn the tab forces forward the vertical plastic ridge as illustrated in FIG. 12. It will be noted that the rigid plastic drive plate 27 is cut in half, the top portion being eliminated in this drawing. The purpose of the drawing is to show the function of the flat plastic pushing mechanism.

In operation the apparatus of FIGS. 1-4 is as follows:

For a right hand person using the I.V., the procedure should be as follows: After locating and preparing the chosen vein, the starter puts gentle traction on the vein with the index finger of his left hand. He then grasps the I.V. placement needle with plastic outside catheter 20 with the right hand in the following manner: Referring to FIG. 1-right thumb on top of backflow chamber 21, middle finger on bottom of 21 and the intracath should be held by these fingertips with the posterior end of the I.V. placement needle with plastic outside catheter resting snugly against the inside fleshy part of the right hand. At this point, the tip of the right index finger is pressed into the upper side of the thumb ½" from the end of the thumb. Now, the starter has a firm hold on the I.V. placement needle with plastic outside catheter and the right index finger is positioned to "fire". The starter inserts the pointed end of the I.V. placement needle with plastic outside catheter needle 23 into the skin, then into the vein to a point where he feels the tip of the teflon catheter 26 is within the vein wall. At this point, the starter freezes—he sees the backflow of blood into the backflow chamber 21 and simply releases the right index finger. The index finger thrusts forward striking the posterior side of the plastic drive plate 27. The plate 27, along with the teflon catheter 24 are projected forward. The teflon catheter tube 26 moves forward on the inside of the vein and the plastic plate 27 remains outside the surface of the skin. The steel needle 23 remains "stationary". The teflon catheter is now safely in position.

The embodiment of FIG. 5 works with the same principle in mind—delivering a quick forward blow to the plastic drive plate 27 to project the teflon catheter tube 26 into the vein without moving the steel needle 23 and with minimal movement of the hands. The starter holds the I.V. placement needle with plastic outside catheter 20 in the following manner: A right handed person grasps shaft 22 with 4 fingers of the right hand; curls these 4 fingers around shaft. Then with the thumbnail or thumb end of right hand, downward pressure is exerted against 30 until it touches 22. When a backflow is obtained, 30 is released by the thumb. It flies back into position striking the plastic drive plate 27, moving it and the teflon catheter tube 26 forward, with the teflon catheter moving forward inside the vein and the plastic drive plate 27 remaining outside the skin. The plastic firing mechanism 29 is made of such plastic material that allows the necessary potential energy needed to deliver such force that is needed to drive the rigid plastic drive plate 27 and the teflon catheter tube 26 forward.

Figure 9:
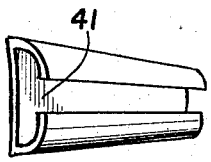
FIGS. 9, 10 and 11 are disassembled views of the hammer mechanism of a modified form of I.V. placement needle with plastic outside catheter shown in FIG. 12.
Figure 10:
Figure 11:
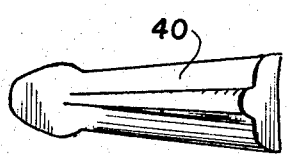

Referring now to FIGS. 6, 7 and 9, the apparatus utilizes a spring loaded plunger 38 which, when released, strikes the rigid plastic drive plate 27, projecting it forward along with the teflon catheter tube 26. The apparatus of FIG. 6 is actually a separate steel or plastic cylinder shaped attachment 33 which fits over the backflow chamber 21 of the apparatus of FIGS. 1-4. It, however, can be used over and over, because it does not have to be sterile and is easily fit on and taken off after each use. To fit over the backflow chamber, 2 separate means can be used; one is by making the inside cylinder shape such that it fits snugly over the backflow chamber 21; the other is by using a band and screw type device which tightens the cylinder around the backflow chamber 21 at both ends.

In operating the embodiment of FIG. 6, when the starter wants to "load and lock in place" he slides the trigger pin 37 to the top of the T and pushes it into either side of the T, depending on whether he is left handed or right handed. If left handed, he slides it into the left side of the T. If right handed, he slides it into the right side of the T. With the continuous pressure exerted by the spring and the shape of the T, the trigger pin 37 can only fire if someone pushes it to the middle of the top of the T.

FIGS. 9, 10, 11 and 12 illustrate a still further embodiment but still keeping the same principles as FIGS. 1 through 8. It is a sliding piece of horizontal plastic 40 that fits in a groove 41 with an elevated thumb tab 42 on the posterior end of the device. The thumb tab 42 can be moved forward with the tip of the index finger and in turn the tab forces forward the vertical plastic ridge as illustrated in FIG. 12. The drawing is to show the function of the flat plastic pushing mechanism.

A right handed starter holds the I.V. placement needle with plastic outside catheter 12 and with right thumb at A and right middle finger at B.

When the backflow is noted, the tip of the index finger pushes the "push in" thumb tab 42 forward. The end of the flat plastic "push in" mechanism 42 is up against the vertical drive plate 27 along with the teflon catheter tube 26, the latter moving forward inside the vein and the vertical drive plate 27 remaining outside the skin. The drive plate 27 may be joined to the catheter hub 25 with a breakaway plane of weakness so once the I.V. has been established and the catheter tube 26 properly in the vein the projecting drive plate can be removed to avoid any patient discomfort.

What I claim is:

1. An I.V. placement needle with plastic outside catheter comprising:
    (a) a backflow chamber within a chamber guard,
    (b) a vein puncture needle in communication with the backflow chamber, (c) a catheter hub, (d) a catheter tube secured to said hub and receivable over said vein puncture needle concentrically therewith, and (e) a plastic drive plate upstanding from said catheter hub and having its major plane transverse to the axis of said hub and catheter tube for engagement by a driving force to advance the hub and catheter tube coaxially over said vein puncture needle, and a resilient potentially biased striking means carried by said backflow chamber guard positioned to when released engage said plastic drive plate and with an energy thrust to advance the catheter tube and its hub axially over the vein puncture needle to cause the catheter tube to be introduced in a vein following entry of the vein puncture needle into the vein.

2. An I.V. placement needle with plastic outside catheter apparatus as claimed in claim 1 wherein said resilient potentially biased striking means is a resilient plastic firing mechanism having a cocking arm and a firing arm.

3. An I.V. placement needle with a plastic outside catheter apparatus as claimed in claim 2 wherein said resilient potentially biased striking means is a spring actuated plunger having a trigger pin riding in a T-shaped slot so that when the pin is moved from either side of the head of the T the compressed spring will drive the plunger forward striking the plastic drive plate upstanding from the catheter hub to drive the catheter tube forward over the vein puncture needle after vein puncture has been established.

* * * * *

UNITED STATES PATENT AND TRADEMARK OFFICE
CERTIFICATE OF CORRECTION

PATENT NO. : 4,292,970
DATED : October 6, 1981
INVENTOR(S) : William M. Hession, Jr.

It is certified that error appears in the above—identified patent and that said Letters Patent is hereby corrected as shown below:

Column 3, line 40, change "intracath" to --I.V. replacement needle with plastic outside catheter--.

Signed and Sealed this

Second Day of March 1982

[SEAL]

Attest:

GERALD J. MOSSINGHOFF

Attesting Officer    Commissioner of Patents and Trademarks